US007332342B2

United States Patent
Kishinami

(10) Patent No.: US 7,332,342 B2
(45) Date of Patent: Feb. 19, 2008

(54) METHOD OF JUDGING SUITABILITY OF RAW BARLEY FOR FEEDSTOCK FOR MALT PRODUCTION ACCORDING TO STAINING TECHNIQUE

(75) Inventor: Isao Kishinami, Gunma (JP)

(73) Assignee: Sapporo Breweries Ltd., Tokyo (JP)

( * ) Notice: Subject to any disclaimer, the term of this patent is extended or adjusted under 35 U.S.C. 154(b) by 0 days.

(21) Appl. No.: 11/524,899

(22) Filed: Sep. 22, 2006

(65) Prior Publication Data

US 2007/0026522 A1 Feb. 1, 2007

Related U.S. Application Data

(62) Division of application No. 10/483,564, filed as application No. PCT/JP03/06534 on May 26, 2003, now Pat. No. 7,129,090.

(30) Foreign Application Priority Data

May 27, 2002 (JP) .............................. 2002-152037

(51) Int. Cl.
  *G01N 33/50* (2006.01)
  *A01C 1/00* (2006.01)
(52) U.S. Cl. ........................... 436/2; 47/14; 47/58.1 R; 436/20
(58) Field of Classification Search ............ 47/58.1 R, 47/58.1 SE, 14; 426/231; 73/7, 866; 436/2, 436/5–6, 20, 174–175
See application file for complete search history.

(56) References Cited

U.S. PATENT DOCUMENTS

| 2,415,734 | A | 2/1947 | Dworschack et al. ......... 435/93 |
| 3,317,402 | A | 5/1967 | Smith et al. ................. 435/185 |
| 3,896,001 | A | 7/1975 | Barrett et al. ................ 435/185 |
| 4,497,799 | A | 2/1985 | Yoshizumi et al. ............ 514/9 |
| 4,931,061 | A | 6/1990 | Young ......................... 47/57.6 |
| 5,628,810 | A * | 5/1997 | Dugast et al. ........ 47/58.1 R X |
| 5,689,054 | A * | 11/1997 | Raboy ................. 47/58.1 R X |
| 5,950,360 | A * | 9/1999 | Heinrich et al. .......... 47/58.1 R |
| 7,087,256 | B2 * | 8/2006 | Gimbel et al. ........... 426/231 X |
| 7,189,677 | B2 * | 3/2007 | Harada et al. ....... 47/58.1 SE X |
| 7,213,367 | B2 * | 5/2007 | Wertz et al. ........ 47/58.1 SE X |
| 2004/0241635 | A1 * | 12/2004 | Buckley .............. 47/58.1 R X |

FOREIGN PATENT DOCUMENTS

JP 56-049342 5/1981

OTHER PUBLICATIONS

Tsuda et al, Nihon Sakumotsu gakkai Kiji, 1998, vol. 67, No. 3, pp. 416-418 (in Japanese).
Aqu et al, Journal of the Institute of Brewing, 2002, vol. 108, No. 2, pp. 215-220.

* cited by examiner

*Primary Examiner*—Thomas P. Noland
(74) *Attorney, Agent, or Firm*—Oblon, Spivak, McClelland, Maier & Neustadt, P.C.

(57) ABSTRACT

An object of the present invention is to provide a method for evaluating the physical strength of husks of a barley ingredient for malt manufacture. Barley kernels with husks are disposed in a sulfuric acid solution with a concentration of approximately 40% to 60%, and are agitated for a prescribed time (e.g. approximately 1 hour) using a stirrer bar or the like. After agitation, the barley kernels are treated with a mixed liquid of Methylene Blue and Eosin, and the degree of peeled husk (remaining degree) is examined by referring to the degree of dyed barley kernels, to thereby evaluate the physical strength of the husks of the barley kernels.

4 Claims, 4 Drawing Sheets

PHOTOGRAPH 1: "RYOFU" PRODUCED IN YEAR 2000 (PEEL RATIO 12%)

PHOTOGRAPH 1: "RYOFU" PRODUCED IN YEAR 2000 (PEEL RATIO 12%)

PHOTOGRAPH 2: "FRANKLIN" PRODUCED IN YEAR 2000 (PEEL RATIO 40%)

PHOTOGRAPH 3: "HARRINGTON" PRODUCED IN YEAR 2000 (PEEL RATIO 18%)

METHOD OF JUDGING SUITABILITY OF RAW BARLEY FOR FEEDSTOCK FOR MALT PRODUCTION ACCORDING TO STAINING TECHNIQUE

TECHNICAL FIELD

The present invention relates to an evaluation method regarding the suitability of barley, being used for malting barley for malt manufacture, and being the malt ingredient for manufacturing beer, low-malt beer, distilled liquor, and the like.

Further, the present invention relates to an evaluation method during selection of a variety• line in growing a barley variety for breeding a barley variety having a husk with desirable physical strength.

BACKGROUND ART

Barley, being the malt ingredient in manufacturing beer, low-malt beer, distilled liquor and the like, becomes the ingredient for malt manufacture by undergoing processes such as harvest• selection• transportation, and having impurities, foreign substances, different type kernels and the like removed therefrom. Barley kernels are subject to various physical forces during such processes in respective stages or during transfer in-between the stages. During this, the husk disposed at the outermost layer of the barley kernel may in some cases peel off from its barley kernel due to the barley kernels being brushed against each other or barley kernels being mechanically struck against hard objects such as metal ones.

Such a barley kernel having its husk peeled off will, in upcoming processes, be subject to a harsher force than that of a barley kernel which is not peeled. In this case, a barley kernel whose embryo is not covered by the husk is particularly vulnerable to embryo damage, thereby preventing the peeled barley kernel from sprouting normally.

Further, in the beginning of malt manufacture, barley kernels are first soaked in water. Barley kernels containing moisture will, however, soften and thereby be more liable to receive damage compared to dry ones.

Malt can be manufactured only after biological• physiological• biochemical reactions take place to sprout the barley. However, barleys that have failed to sprout not only are unable to malt, but also cause corrosion during the sprouting stage, adversely affect normal sprouted barley, and result in a final product with a malt quality that is unsuitable for its intended use.

Since evaluation of whether the barley ingredient is suitable for malt manufacture was conventionally performed through macroscopic testing by engineers experienced in malt manufacture, there was a discrepancy in the evaluation results depending on the individual performing the evaluation, and the accuracy of the results was not always high.

In respect of barleys aimed to be purchased for malt manufacture, the present invention enables distinct evaluation of whether the barleys are suited for malt manufacture with a scientific method without relying on experience by using a portion of the barleys prior to their purchasing. Further, the present invention provides a method of selecting kernels of barley used in breeding a malt, which have a husk of high physical strength, suited for malt manufacture.

DISCLOSURE OF INVENTION

The above-mentioned problems can be solved with the following processes according to the present invention.

One embodiment of the present invention is a method having a characteristic in which solubilization of husk is performed by uniformly sampling barley, aimed to be used as an ingredient, and treating the obtained sample ingredient with sulfuric acid. Then, the barley kernel having the solubilized husk is agitated under prescribed conditions. Observations are made on the degree of peeled husk or the degree of remaining husk of the barley kernel subsequent to the agitation. According to the results, the physical endurance of the husk of the barley kernel is evaluated. Thereby, physical strength of the husk of the barley can be objectively determined. Therefore, a high quality barley ingredient for malt manufacture aimed for manufacturing fermented malt beverages can be provided.

Another embodiment according to the present invention allows barley kernels with peeled off husks and also the peeling degrees of the barley kernels to be distinctively determined by performing a dyeing process to barley kernels that have undergone the above-described solubilization with sulfuric acid and agitation. Thereby, physical strength of husks can be evaluated with higher accuracy. Further, since the portion at which husks remain and the portion at which husks are peeled are distinguishable by color, observation through the naked eye will be easier, and automatic quality distinction will also be possible by using image signals of a camera tube and the like.

Furthermore, in another embodiment according to the present invention, the proportion of barley kernels having 80% or more of its husk for a single kernel being peeled to the total barley kernels is used as a criterion for evaluating whether the barley, having undergone husk solubilization and agitation according to the present invention, is suited to be the barley ingredient for malt manufacture. Thereby, the quality of barley ingredient can be classified according to a uniform criterion, and high quality malt manufacture can be achieved.

A further embodiment according to the present invention is a method using the above-described barley ingredient evaluation method during selection in growing a barley variety and breeding the barley variety.

All of the barley ingredient evaluation methods according to the present invention may be employed for selection of seeds used in breeding barley, as an alternative for straightforwardly employing the methods for malt manufacture. Thereby, barley that has a husk with strong physical strength can be bred, and a high quality barley ingredient for malt manufacture can be provided.

BEST MODE FOR CARRYING OUT THE INVENTION

Embodiments of an evaluation method for evaluating the physical strength of a barley husk according to the present invention are described in detail below.

The barleys, the reagents, and the testing methods employed in the embodiments according to the present invention are given below. Barley "Ingredient and Reagent"

1. Ingredient
   - 1-1: Malting barley "RYOFU" (Produced in Hokkaido in year 2000)
   - 1-2: Malting barley "FRANKLIN" (Produced in Australia in years 1999-2000)
   - 1-3: Barley "HARRINGTON" (Produced in Canada in year 1998)
2. Reagent
   - 2-1: 50% Sulfuric Acid
   - 2-2: 0.2% Methylene Blue+0.2% Eosin Y (98% Methanol Solution)

"Method"

(1) Sample approximately 4 g of barley (approximately 100 kernels) from an ingredient lot. Add the samples to a 200 ml beaker containing 80 ml (room temperature) of 50% sulfuric acid. Agitate for 1 hour at 150 rpm by using a 5 cm long stirrer bar and make the husk easy to peel off.

(2) After the agitation, dye the barley, which is washed with water, for 1 hour with 0.2% Methylene Blue+0.2% Eosin Y (98% Methanol Solution). Remove excess dye by washing with water.

(3) The husk and pericarp remaining after the sulfuric acid process are dyed to a dark blue color, and the embryo and the scutellum is dyed to a red-pink color. Exposed endosperm is not dyed and is a white color.

Figure 1:
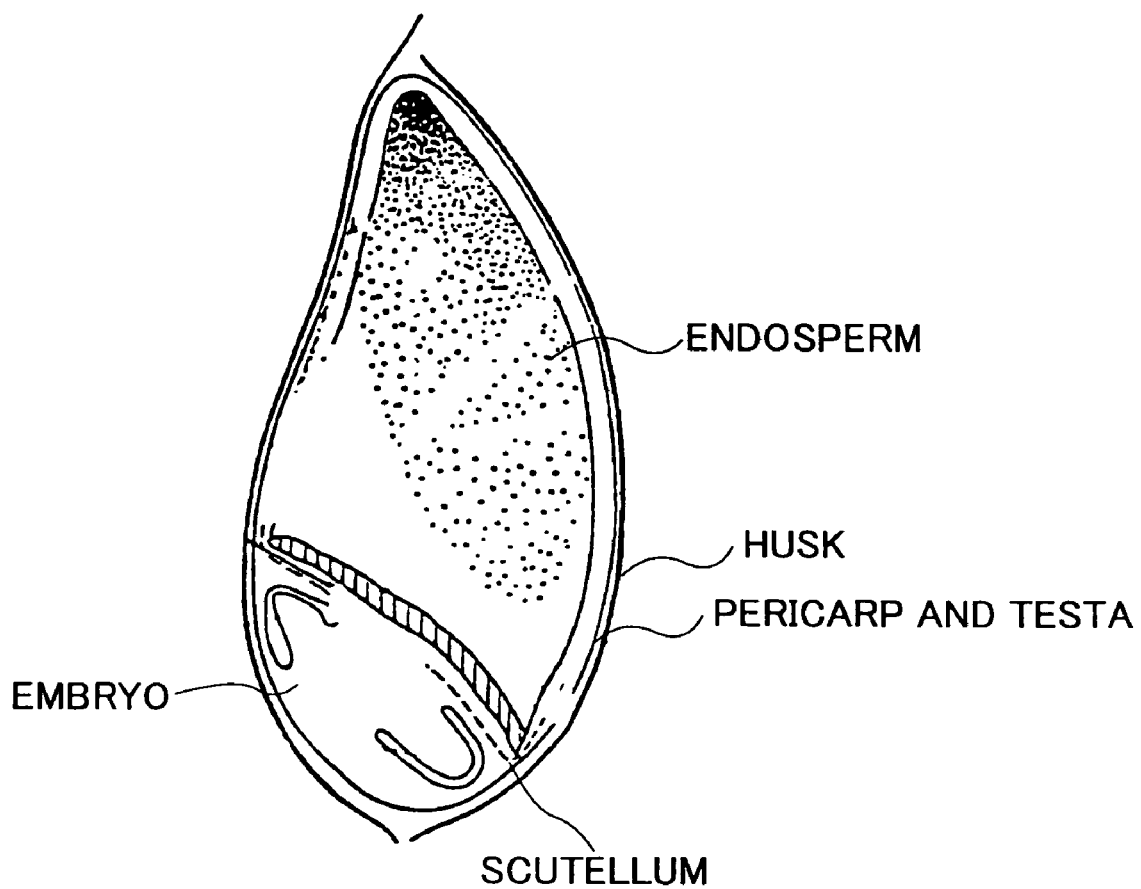
FIG. 1 is a view for explaining a cross-sectional structure of barley.

FIG. 1 shows a cross-sectional structure of a barley kernel where the kernel is in a state completely covered by a husk.

Figure 2:
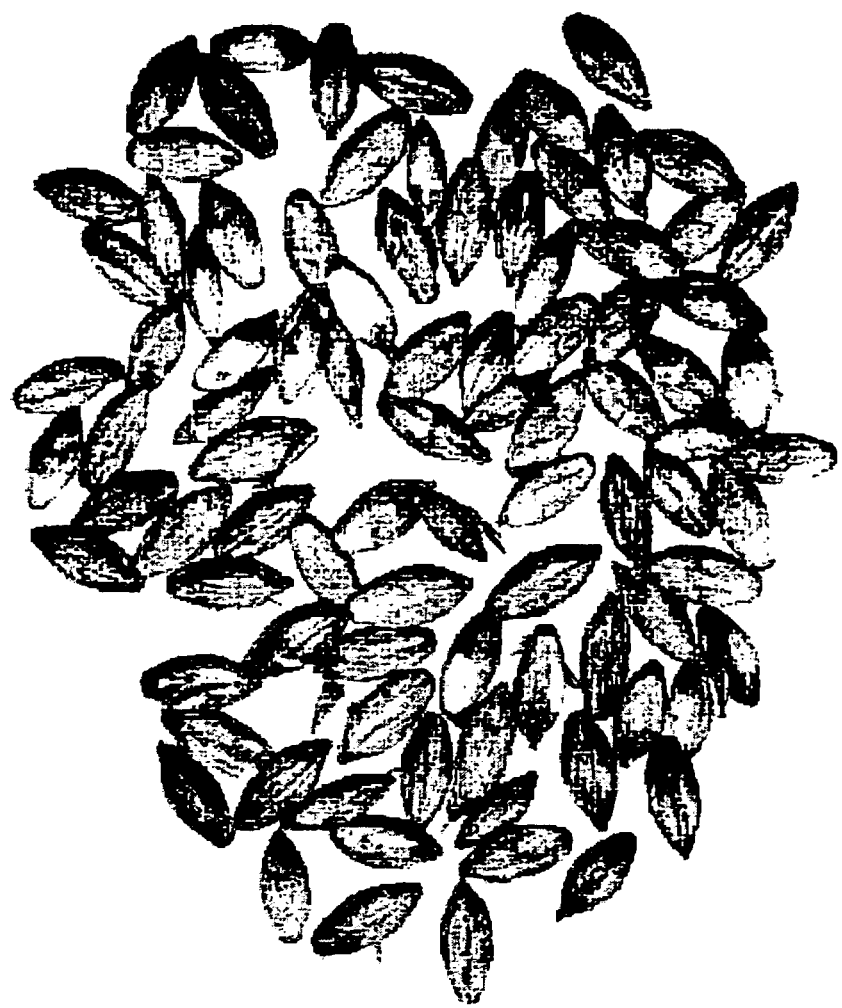
FIG. 2 is an image showing an example of malting barley "RYOFU" with a method according to the present invention applied.
Figure 3:
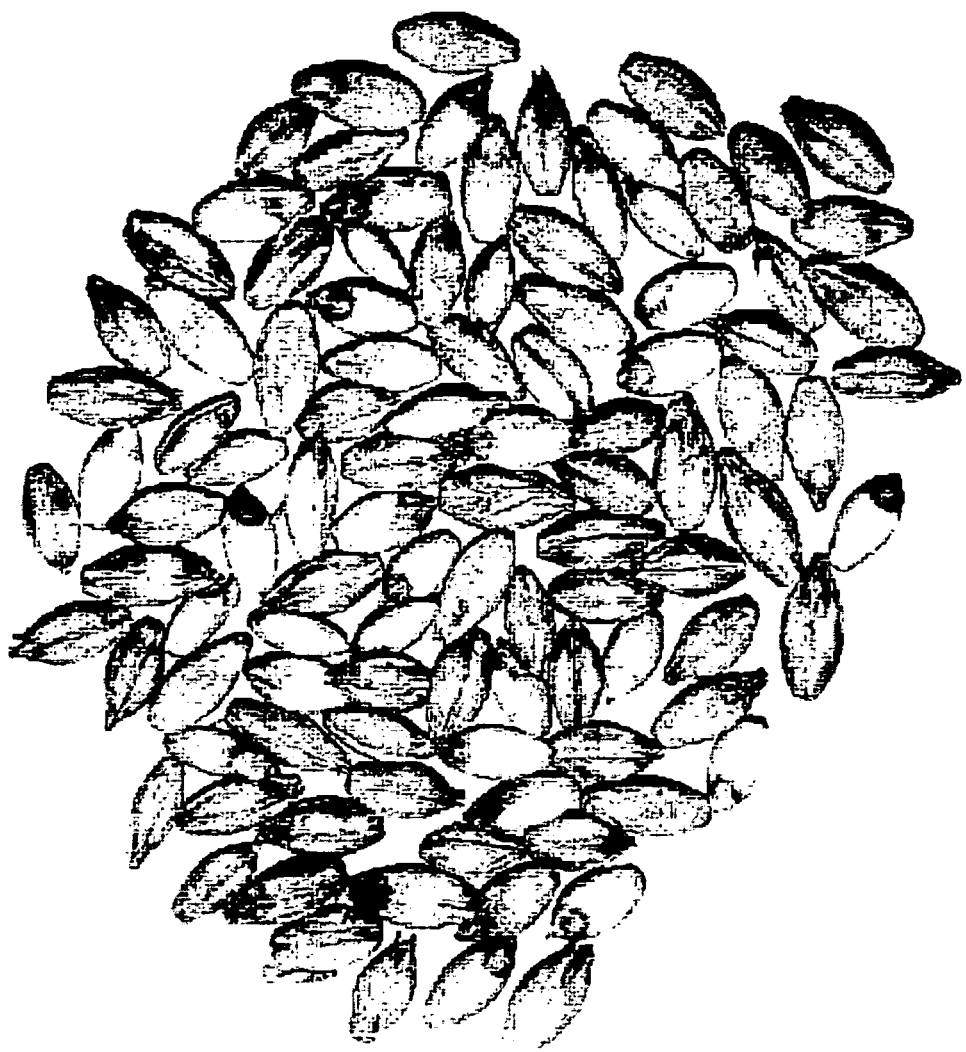
FIG. 3 is a view showing an example of malting barley "FRANKLIN" with a method according to the present invention applied.
Figure 4:
FIG. 4 is a view showing an example of barley "HARRINGTON" with a method according to the present invention applied.

FIGS. 2, 3, and 4 are photographs showing the results of performing the method on barley "RYOFU", barley "FRANKLIN", and barley "HARRINGTON", respectively.

"Method of Evaluating Ease of Peeling of Barley Husk"

When barley kernels, having been treated with sulfuric acid, are dyed with the two dyes, the remaining husk and pericarp are dyed to a dark blue color, and the embryo and the scutellum are dyed to a red-pink color, as described above.

It is believed that the reason why the husk and the embryo are dyed to different colors in the foregoing manner is because the large amount of cell membrane in the husk causes it to be dyed to blue color, and the large amount of plasma in the embryo (surface) causes it to be dyed to red-pink color.

Accordingly, in order to observe the physical endurance of the husk subjected to sulfuric acid treatment and agitation, the portion where husk is peeled and the portion where husk remains can be distinctively confirmed by counter staining the treated kernels with the two dyes. Furthermore, whether the essential embryo, in particular, is exposed can be distinctively determined depending on whether the embryo is dyed to red-pink color (embryo; eosin-Y).

The photograph in FIG. 2 shows barley "RYOFU" dyed with the present method. "FRANKLIN" (FIG. 3) and "HARRINGTON" (FIG. 4), which are said to be varieties susceptible to husk peeling, are shown for comparison. As is apparent in the photographs, "FRANKLIN" lacks physical endurance of husks, and a large number of kernels being dyed to white and red-pink color have been observed more in "FRANKLIN" than in other samples.

Here, in the present embodiment, the ratio of peeled husk, after being subjected to the treatment according to the present invention (peel ratio), is obtained and quantified as an index representing the physical strength (endurance) of husk. That is, after sulfuric acid treatment and agitation, the proportion (%) of kernels having 80% or more of husk for a single kernel being peeled to the total number of kernel samples is obtained and quantified as peel rate R, to thereby serve as an index of physical strength of the husk.

In the above-described example of performing the method on the 3 varieties of barley, "RYOFU" produced in year 2000 (FIG. 2) had a 12% peel ratio. On the other hand, "FRANKLIN" produced in year 2000 (FIG. 3) had a 40% peel ratio. Further, "HARRINGTON" produced in year 1998 had an 18% peel ratio.

Accordingly, by obtaining the peel ratio and using it as an index of the physical strength of the husk, objectiveness can be attained in determining whether the barley ingredient is suited for malt manufacture, and accurate quality control of the barley ingredient can be achieved.

It is to be noted that, in the present embodiment, according to the criterion for evaluating the barley ingredient with respect to the ratio (%) of kernels having 80% or more of husk (embryo side) being peeled, it is evaluated that ① for 20% or less: no problems, ② for 20% to 35%: caution required in use, and ③ for 36% or more: unsuitable for malt manufacture. These are defined by relating the results based on experience with respect to the results of peel ratio (%) according to the present method.

It is to be noted that, obviously, even where the same barley is used, the degree of peeling that the barley kernels experience will be different depending on the equipment that is used.

Accordingly, with use of the present method, prior to being accepted by a factory, the degree of the physical endurance of the husk of the barley kernels in each acceptance lot can be easily distinguished and objective evaluation results can be attained, thereby providing for high quality malt manufacture.

It is to be noted that, although approximately 100 sampled kernels are added to a 200 ml beaker containing 80 ml (room temperature) of 50% sulfuric acid and agitated for 1 hour at 150 rpm by using a 5 cm long stirrer bar in the above-described example, treatment conditions are not to be limited to such. For example, the concentration of the sulfuric acid may range from approximately 40% to 60%. Further, agitation conditions, such as rotation count or agitation time, may differ depending on the number of sampled kernels with respect to the volume of the sulfuric acid solution, and, therefore, may be changed accordingly. Nevertheless, since observation of the endurance of agitated husk is necessary, an accurate evaluation cannot be executed if agitation time is too short. Therefore, the preferred agitation time is more or less 1 hour (approximately 40, 50 minutes to 60, 70 minutes).

Further, although the above-described example is explained as a method for evaluating the degree of the physical strength of the husk of the barley ingredient before being accepted into the malt manufacture stage, the evaluation method is not limited to evaluating barley ingredient that is straightforwardly used in barley manufacture, but can obviously be employed in evaluating suitability in selecting seeds for growing a barley variety. For example, a barley variety, where 20% or less is the proportion (%) of kernels having 80% or more of husk (embryo side) being peeled, may be chosen as a seed for breeding a barley variety, to thereby breed a barley variety suitable for malt manufacture.

With the present invention, the physical strength of the husk of barley kernels can be objectively determined, and therefore, a high quality barley ingredient for manufacturing malt for fermented malt beverages can be provided.

Further, by performing the dyeing process on barley kernels that have undergone solubilization with sulfuric acid and agitation, barley kernels with peeled husks and the degree of the peeling can be distinctively determined.

Further, the proportion (%) of kernels having 80% or more of husk being peeled, is employed as a criterion for evaluating whether barley, having undergone husk solubilization and agitation, is suitable for malt manufacture. Thereby, the quality of barley ingredient can be classified according to a uniform criterion, evaluation can be performed objectively, and high quality malt manufacture can be achieved.

Further, the evaluation method of the physical strength of the husks of kernels according to the present invention can be employed in selection for growing a variety, to thereby breed a barley variety suitable for malt manufacture.

The invention claimed is:

1. A barley ingredient quality evaluation method for evaluating whether or not a barley ingredient is suited for malt manufacture based on proportion R, R being the proportion of barley kernels having 80% or more of husk for a single kernel being peeled to the total barley kernels, in which the proportion R is computed with samples extracted from the barley ingredient by a method comprising disposing barley kernels with husks in a sulfuric acid solution having a 40% to 60% concentration, agitating the solution having the barley kernels disposed therein for a prescribed time, and observing the degree of husk remaining on the barley kernels subsequent to the agitation.

2. The barley ingredient quality evaluation method as claimed in claim 1, wherein when the proportion R is ① 20% or less: the barley ingredient is evaluated as usable for malt manufacture, ② 20% to 35%: the barley ingredient is evaluated as caution is required during use, and ③ 36% or more: the barley ingredient is evaluated as unusable for malt manufacture.

3. A method of breeding a barley variety comprising:
evaluating barley ingredient quality based on proportion R, R being the proportion of barley kernels having 80% or more of husk for a single kernel being peeled to the total barley kernels, in which the proportion R is computed with samples extracted from the barley ingredient by a method comprising disposing barley kernels with husks in a sulfuric acid solution having a 40% to 60% concentration, agitating the solution having the barley kernels disposed therein for a prescribed time, and observing the degree of husk remaining on the barley kernels subsequent to the agitation;
selecting the barley ingredient from the evaluation results; and
breeding the selected barley ingredient.

4. The method of breeding the barley variety according to claim 3, wherein the selected barley ingredient has the proportion R evaluated as 20% or less.

* * * * *